United States Patent [19]

Yahagi et al.

[11] Patent Number: 4,668,967

[45] Date of Patent: May 26, 1987

[54] FLUORAN COMPOUND AND COLOR FORMING RECORD MATERIALS USING THE SAME

[75] Inventors: Masakichi Yahagi, Tokyo; Takeo Obitsu, Omiya; Tetsuo Igaki, Kawagoe; Kazuyuki Horisawa, Tokyo; Morio Nanbu, Fujimi; Kimiaki Kinoshita, Kitamoto; Sumio Manaka, Tokyo, all of Japan

[73] Assignee: Shin Nisso Kako Co., Ltd., Tokyo, Japan

[21] Appl. No.: 867,837

[22] Filed: May 28, 1986

[30] Foreign Application Priority Data

Jun. 5, 1985 [JP] Japan .................. 60-120633

[51] Int. Cl.$^4$ .................. B41M 5/16; B41M 5/18; B41M 5/22

[52] U.S. Cl. .................. 346/221; 427/151; 549/224; 549/225

[58] Field of Search .................. 346/204, 217, 221; 427/150, 151; 549/224, 225

[56] References Cited

U.S. PATENT DOCUMENTS 4,612,558  9/1986  Anzai et al. .................. 346/221
4,613,879  9/1986  Yahagi et al. .................. 346/221

*Primary Examiner*—Bruce H. Hess
*Attorney, Agent, or Firm*—Armstrong, Nikaido, Marmelstein & Kubovcik

[57] ABSTRACT

3-N-isobutyl-ethylamino-7-phenylaminofluoran is a new green color former. It is used, together with an acidic substance, in color forming record materials for use in pressure sensitive copying paper, heat-sensitive recording paper and the like.

5 Claims, No Drawings

FLUORAN COMPOUND AND COLOR FORMING RECORD MATERIALS USING THE SAME

FIELD OF THE INVENTION

This invention relates to 3-N-isobutyl-ethylamino-7-phenylaminofluoran which forms green color upon contact with an acidic substance, and to color forming record materials using the fluoran compound as a color former.

BACKGROUND OF THE INVENTION

Record materials comprising dyes (color former) which are colorless or substantially colorless in themselves but form colors upon contact with an acidic substance (color developer) have been extensively used for a pressure-sensitive copying paper, a heat-sensitive recording paper and the like. For the record materials, black color formers have been used mainly, but green color formers are sometimes used in combination therewith to adjust the hue of black colors. On that account, it is strongly desired that green color formers also exhibit excellent fastness before and after color formation. Further, the speedup of the services of communication recording devices such as facsimile requires increase in the color forming speed of the heat-sensitive recording papers used therefor. In this connection, there is a pressing need to improve color forming property of the green color formers used in admixture with the black color formers.

As green color formers, 3-diethylamino-5-methyl-7-dibenzylaminofluoran of the formula (referred to hereafter as "Compound A"),

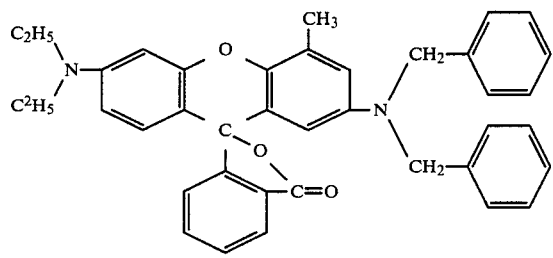

and 3-pyrrolidino-7-phenylaminofluoran of the formula (referred to hereafter as "Compound B"),

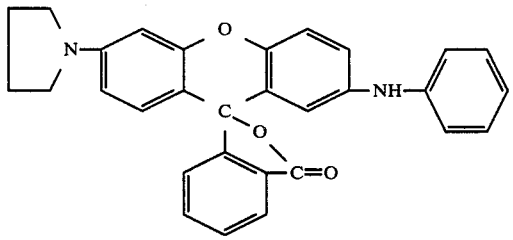

have been disclosed respectively in Japanese Patent Publication No. 34044/1974 and Japanese Patent LOP Publication No. 9430/1975 or No. 82127/1975 and they have been put to practical use. However, these fluoran compounds are not satisfactory in respect of the fastness.

SUMMARY OF THE INVENTION

Therefore, it is a principal object of this invention to provide green color formers having excellent fastness.

Another object of this invention is to provide a color forming record material using said dyes.

Other objects of this invention will become apparent from the following description.

These objects are achieved by providing as a green color former 3-N-isobutyl-ethylamino-7-phenylaminofluoran of the formula

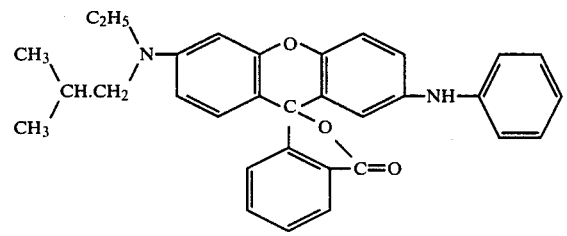

DETAILED DESCRIPTION OF THE INVENTION

According to one aspect of this invention, there is provided a color forming record material which comprises a substrate, an acidic substance and 3-N-isobutyl-ethylamino-7-phenylaminofluoran as a color former.

In another aspect, this invention provides a method of recording by development of color which comprises bring 3-N-isobutyl-ethylamino-7-phenylaminofluoran into intimate contact with an acidic substance.

The fluoran compound of the invention exhibits excellent light fastness in color forming record materials. The remarkable effects of the present fluoran compound are demonstrated in pressure-sensitive copying papers, especially when a top sheet bearing said compound thereon is exposed to light irradiation before the use thereof. To verify such effects, a light fastness test wherein the top sheet of the pressure-sensitive copying paper is exposed to light irradiation for 60 minutes, is carried out to compare the present compound (dark green color former) with the prior compound A (green color former) and the prior compound B (dark green color former). The top sheets used in this test are respectively prepared by use of the present compound as well as the prior Compounds A and B according to the procedures mentioned later in Example 2 and Comparative Example 1. Subsequently, each of the top sheets with or without exposure to light irradiation is superposed onto a bottom sheet and a pressure is applied to the superposed sheets to develop color on the surface of the bottom sheet. The density and hue of the developed color are measured by a color difference meter. The results are shown in Table 1.

TABLE 1

|  |  | Before Test | After Test | ΔL,Δa,Δb | ΔE |
|---|---|---|---|---|---|
| Present Compound | L | 46.64 | 52.47 | 5.38 | |
|  | a | −10.74* | −9.62* | 1.12 | 5.98 |
|  | b | 7.39 | 8.07 | 0.68 | |
| Compound A | L | 48.23 | 56.15 | 7.92 | |
|  | a | −14.96* | 5.39 | 20.35 | 20.26 |
|  | b | 9.93 | 3.40 | −6.52** | |
| Compound A | L | 42.13 | 67.28 | 25.14 | |
|  | a | −9.08* | −3.77* | 5.30 | 25.84 |

TABLE 1-continued

| | Before Test | After Test | ΔL,Δa,Δb | ΔE |
|---|---|---|---|---|
| b | 5.32 | 2.53 | −2.79** | |

In the table, the value "L" represents brightness. The smaller value "L" means the deeper color. The value "a" represents hue wherein the positive value shows a degree of reddish hue and the negative value* shows a degree of greenish hue. The larger absolute values of "a" and "b" mean the deeper hue. The value "b" represents hue wherein the positive value shows a degree of yellowish hue and the negative value** shows a degree of bluish hue. ΔL, Δa and Δb individually represent differences between the values of L, a and b as measured before and after the light fastness rest and ΔE represents a total value of the changes in brightness and hue.

In the table, the change in the value "a" of the compound A from −14.96 to 5.39 indicates the ract that the developed color on the pressure-sensitive copying paper before the light fastness test was green, whereas tne developed color after the test has changed from green to reddish color, as shown in the value "Δa" which is as high as 20.35.

In the case of the compound B, though such marked change in hue of the developed color before and after the light irradiation as in the compound A was not observed, an increase of the value "L" from 42.13 to 67.28 as measured after the light irradiation indicates the fact that the density of green color developed by the compound B on the paper has become markedly pale due to the light irradiation.

In conclusion, the results of visual observation of the developed color on the pressure-sensitive copying paper before and after the light fastness test are well in agreement with the measured results as shown in the above table. That is, the color hue developed by the compound A on the paper after the light fastness test becomes reddish (pale reddish-brown color), and though no marked change in color hue developed by the compound B on the paper before and after the light fastness test is observed, the green color density after the test becomes so markedly small that the paper bearing such a color is of little practical use as a pressure-sensitive copying paper.

In contrast thereto, the changes due to the light fastness test in the values of "L", "a" and "b" of the present compound are slight, and even after the test, the developed color is found still green and, of course, the density of the green color developed by the present compound on the paper is sufficiently maintained at a level for fulfilling the purpose of using said paper as a pressure-sensitive copying paper.

Likewise, the relationship between the changes of hue and color density due to light irradiation is observed when the clay coated bottom sheet is substituted for the phenol-formalin resin coated botton sheet used in Example 2 below as well as in Comparative Example 1 below.

The present fluoran compound also exhibits excellent properties when used in heat-sensitive recording papers. The test results obtained on the heat-sensitive recording papers as prepared in Example 5 below and Comparative Example 2 below are shown in Table 2, wherein the measured values include those of whiteness of the coated surface of paper as prepared, those of densities of color developed on the coated surface when heated to 150° C., and those of color densities of those coated surfaces before and after subjecting to the moisture and heat resistance test and to the light fastness test. The results shown in Table 2 indicate that when the present fluoran compound as well as the prior compounds A and B are used in heat-sensitive recording papers, the present compound is superior to both compounds A and B in whiteness of the coated surface as prepared, densities of colors developed by heating on the coated surface, and in resistance to moisture and heat as well as in light fastness.

TABLE 2

| | Before color development | | | After color development | | |
|---|---|---|---|---|---|---|
| | Coated surface | After moisture and heat resistance test | After light fastness test | Developed color density | After moisture and heat resistance test | After light fastness test |
| Present Compound | 0.07 | 0.08 | 0.18 | 1.27 | 1.21 | 1.16 |
| Compound A | 0.14 | 0.18 | 0.45 | 1.22 | 1.20 | 0.98 |
| Compound B | 0.12 | 0.13 | 0.22 | 1.22 | 1.18 | 1.10 |

In the tests conducted above, Wratten #47 Filter was used for the measurement of color density after the light fastness test, and Wratten #25 filter was used for other measurements.

The fluoran compound of the present invention is prepared in a usual manner by reacting one mole of o-(4-N-isobutyl-ethylamino-2-hydroxy)benzoylbenzoic acid of the formula

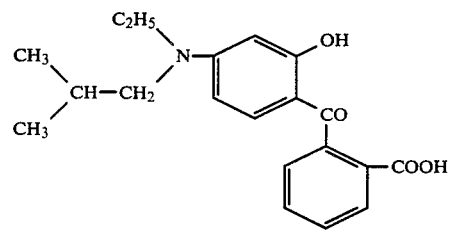

with approximately one mole of 4-lower alkoxy diphenylamines in sulfuric acid. The concentration of sulfuric acid used is preferably 80% or higher and the reaction temperature is desirably 35° C. or lower. The reaction time requires about 48 hours when the reaction temperature is from 20° C. to 25° C.

The fluoran compound of the present invention can be used singly for the preparation of record materials which form green color. Further, it may be used in admixture with any other color formers e.g., the black color formers slightly tinged with red or the black color formers which are tinging with red due to light fading, thereby to develop a color as close to black as possible. Furthermore, the present compound can be used in admixture with blue color formers and red color formers to prepare a record material which forms black color.

Black color formers which are usable in admixture with the present fluoran compound include, by way of only illustration but not limitation, those which are listed below.

3-Dimethylamino-6-methyl-7-phenylaminofluoran
3-Diethylamino-6-methyl-7-phenylaminofluoran
3-Diethylamino-6-methyl-7-xylidinofluoran
3-Diethylamino-6-methyl-7-p-butylphenylaminofluoran
3-Diethylamino-6-methyl-7-anisidinofluoran
3-Dipropylamino-6-methyl-7-phenylaminofluoran
3-Di-n-butylamino-6-methyl-7-phenylaminofluoran
3-N-Isopropyl-methylamino-6-methyl-7-phenylaminofluoran
3-N-Isobutyl-ethylamino-6-methyl-7-phenylaminofluoran
3-N-Isopentyl-ethylamino-6-methyl-7-phenylaminofluoran
3-N-Hexyl-ethylamino-6-methyl-7-phenylaminofluoran
3-Dibenzylamino-6-methyl-7-phenylaminofluoran
3-N-Methyl-cyclohexylamino-6-methyl-7-phenylaminofluoran
3-N-Methyl-cyclohexylamino-5-chloro-6-methyl-7-phenylaminofluoran
3-N-n-Pentyl-cyclohexylamino-6-methyl-7-phenylaminofluoran
3-N-Methyl-p-tert-butylcyclohexylamino-6-methyl-7-phenylaminofluoran
3-N-Ethyl-3',3',5'-trimethylcyclohexylamino-6-methyl-7-phenylaminofluoran
3-N-Ethyl-furfurylamino-6-methyl-7-phenylaminofluoran
3-Pyrrolidino-6-methyl-7-phenylaminofluoran
3-Piperidino-6-methyl-7-toluidinofluoran
3-Morpholino-6-methyl-7-p-butylphenylaminofluoran
3-N-Methyl-phenylamino-6-methyl-7-phenylaminofluoran
3-N-Ethyl-phenylamino-6-methyl-7-p-toluidinofluoran
3-N-Ethyl-p-toluidino-6-methyl-7-phenylaminofluoran
3-α-Naphthylamino-6-methyl-7-phenylaminofluoran
3-Dimethylamino-7-N-benzyl-m-trifluoromethylphenylaminofluoran
3-Diethylamino-7-m-trifluoromethylphenylaminofluoran
3-Diethylamino-5-ethyl-7-m-trifuloromethylphenylaminofluoran
3-Diethylamino-5-ethyl-7-m-trifluoromethylphenylaminofluoran
3-Diethylamino-5-chloro-7-m-trifluoromethylphenylaminofluoran
3-Dipropylamino-7-m-trifluoromethylphenylaminofluoran
3-Di-n-butylamino-7-m-trifluoromethylphenylaminofluoran
3-N-Ethyl-p-toluidino-7-m-trifluoromethylphenylaminofluoran
3-Piperidino-7-m-trifluoromethylphenylaminofluoran
3-Pyrrolidino-7-m-trifluoromethylphenylaminofluoran
3-Morpholino-7-m-trifluoromethylphenylaminofluoran
3-N-Methyl-cyclohexylamino-7-m-trifluoromethylphenylaminofluoran
3-N-Benzyl-cyclohexylamino-7-m-trifluoromethylphenylaminofluoran
3-N-Ethyl-furfurylamino-7-m-trifluoromethylphenylaminofluoran
3-N-Ethyl-furfurylamino-6-methyl-7-m-trifluoromethylphenylaminofluoran
3-Diethylamino-7-chlorophenylaminofluoran
3-Diethylamino-7-bromophenylaminofluoran
3-Diethylamino-6-chloro-7-phenylaminofluoran
3-Di-n-butylamino-7-chlorophenylaminofluoran
3-Diethylamino-6-methyl-7-benzylamino-4',5'-benzofluoran
3-N-Methyl-phenylamino-5,6-benzo-7-phenoxyphenylaminofluoran
3-N-Benzyl-phenylamino-5,6-benzo-7-phenoxyphenylamino-3',4',5',6'-tetrachlorofluoran
3-Diethylamino-7-piperidinofluoran
2-Methyl-3-ethylamino-5,6-benzo-7-phenylaminofluoran
3-Diethylamino-6-methyl-7-(α-phenylethylamino)fluoran
3-Dimethylamino-7-(α-phenylethylamino)fluoran
3-N-Butyl-xylidino-6-methyl-7-benzylaminofluoran
3-Pyrrolidino-7-di(p-chlorophenyl)methylaminofluoran
3-Methylpiperidino-7-di(p-chlorophenyl)methylaminofluoran
3-Morpholino-5,6-benzo-7-phenylaminofluoran
3-N-Methyl-cyclohexylamino-5,6-benzo-7-α-naphthylamino-4'-bromofluoran.

Blue color formers which are usable in admixture with the present fluoran compound include, by way of only illustration but not limitation, those which are listed below.

Crystal violet lactone[3,3-bis(4-dimethylaminophenyl)-6-dimethylaminophthalide],
Benzoyl leucomethylene blue,
5(or 7)-(1-octyl-2-methylindol-3-yl)-5(or 7)-(4-diethylamino-2-ethoxyphenyl)-5,7-dihydrofuro (3,4-b)-pyridine-7(or 5)-one.

Red color (including vermilion, orange and pink) formers which are usable in admixture with the present fluoran compound include, by way of only illustration but not limitation, those which are listed below.

3-diethylamino-6-methyl-7-chlorofluoran,
3-diethylamino-7-chlorofluoran,
3-diethylamino-7-phenylfluoran,
3-diethylamino-7,8-benzofluoran,
3-di-n-butylamino-6-methyl-7-chlorofluoran,
3-N-isobutyl-ethylamino-6-methyl-7-chlorofluoran,
3-N-isobutyl-ethylamino-7-chlorofluoran,
3-N-isobutyl-ethylamino-7,8-benzofluoran,
3-cyclohexylamino-6-chlorofluoran,
3-cyclohexylamino-7-methylfluoran.

The substrate used for the color forming record materials of this invention includes paper, synthetic fiber fabrics, non-woven fabrics, synthetic papers or synthetic resin sheets (e.g., transparent polyethylene sheet).

In addition to heat-sensitive recording papers and pressure-sensitive copying papers mentioned above, color forming record materials of the invention which comprise the present fluoran compound and the mixture thereof with other color formers can be used for, e.g., recording papers relying on heat-sensitive transfer, electro thermo-sensitive recording papers, papers for electrophotography using toners containing acid substances as developers, ultrasonic wave recording paper, photosensitive printing materials, electron recording paper, stamping materials, stamp ink, typewriter ribbons or the like, but not limiting thereto.

Following substantially the same manner as in the case of conventional fluoran compounds, the fluoran compound of this invention can be used to prepare pressure-sensitive copying paper in accordance with such procedures as disclosed in U.S. Pat. Nos.

2,548,365; 2,548,366; 2,800,457 and 2,800,458, Japanese Patent L-O-P Publn. No. 112041/1983 or 139738/1983.

The pressure-sensitive copying paper may be a unit comprising a top sheet wherein microcapsules encapsulating a solution of the color formers in an organic solvent are coated onto the lower surface, and a bottom sheet wherein an acidic substance (a color developer) is coated onto the upper surface (optionally, the unit may be provided with a middle sheet bearing the acidic substance on the upper surface and microcapsules on the lower surface), or a self-contained paper wherein microcapsules and the acidic substance are coated onto the same surface of the paper.

As the organic solvent can be used nonvolatile materials which dissolve the color formers and are inert thereto, for instance, diphenylmethanes, alkyl naphthalenes or alkyl triphenyls.

Acidic substances (color developers) used in this invention may be those as previously known, for example, inorganic acidic substances such as acid clay, activated clay, attapulgite, bentonite, colloidal silica, aluminum silicate, magnesium silicate, zinc silicate, tin silicate, calcined kaolin and talc; aromatic carboxylic acids, such as benzoic acid, p-tert-butylbenzoic acid, phthalic acid, gallic acid, salicyclic acid, 3-isopropyl-salicyclic acid, 3-phenylsalicyclic acid, 3-cyclohexyl-salicyclic acid, 3,5-di-tert-butylsalicyclic acid, 3-methyl-5-benzylsalicyclic acid, 3-phenyl-5-(2,2dimethylbenzyl)salicyclic acid, 3,5-di-(2-methylbenzyl)salicyclic acid and 2-hydroxy-1-benzyl-3-naphthoic acid; salts of these aromatic carboxylic acids with such metals as zinc, magnesium, aluminum, titanium and the like; phenol resin type developers such as p-phenylphenol-formalin resins and p-butylphenol-acetylene resins; and mixtures of these phenol resin type developers and the above-mentioned metal salts of aromatic carboxylic acids.

Following the same manner as in the case of known color formers, heat-sensitive recording papers using the fluoran compound of this invention can be prepared in accordance with such procedures as disclosed, for example, in Japanese Patent Publns. Nos. 27579/1964, 4160/1968 and 14039/1970, or Japanese Patent L-O-P Publn. No. 7087/1984. More particularly, heat-sensitive recording papers excellent in color forming properties can be prepared by coating onto the surface of papers a suspension containing fine particles of the present fluoran compound or mixtures thereof with other color formers and acidic substances in an aqueous solution of water-soluble binders, followed by drying. Furthermore, there can be prepared heat-sensitive recording papers having very high sensitivity when sensitizers are added to the above-mentioned suspension. This suspension may further contain fillers, dispersing agents, colored image stabilizers, antioxidants, desensitizers, anti-tack agents, defoaming agents, light stabilizers, optical brighteners or the like.

Acidic substances (color developers) used for the heat-sensitive recording papers include, for example, bisphenol compounds such as bisphenol A, 4,4'-secondary-butylidene-bisphenol, 4,4'-cyclohexylidenebisphenol, 2,2'-dihydroxy-diphenyl and pentamethylene-bis(4-hydroxybenzoate); sulfur containing bisphenol compounds such as 1,7-di(4-hydroxy-phenylthio)-3,5-dioxaheptane; 4-hydroxybenzoic acid esters such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxy-benzoate and diphenylmethyl 4-hydroxybenzoate; hydroxy-sulfones such as 4-hydroxy-4'-methyldiphenylsulfone, 4-hydroxy-4'-isopropoxydiphenylsulfone and 4-hydroxy-4'-butoxydiphenyl-sulfone; 4-hydroxyphthalic acid diesters such as dimethyl 4-hydroxyphthalate, dicyclohexyl 4-hydroxyphthalate and diphenyl 4-hydroxyphthalate; such esters of hydroxynaphthoic acid as 2-hydroxy-6-carboxyhaphthalene; and further hydroxyacetophenone, p-phenylphenol, benzyl 4-hydroxyphenylacetate, p-benzylphenol, hydroquinone-mono-benzyl ether or the like.

The water soluble binders include, by way of illustration but not limitation, for example, polyvinyl alcohol, hydroxyethyl cellulose, carboxymethyl cellulose, salts of styrene-maleic anhydride copolymers, styrene-butadiene emulsions, vinyl acetate-maleic anhydride emulsions, polyacrylates, polyacrylamide, starches, casein and gum arabic.

The fillers include, for example, clay, talc, kaolin, satin white, titanium oxide, calcium carbonate, magnesium carbonate, barium sulfate, magnesium silicate and aluminum silicate, etc.

The sensitizers include, for example, higher fatty acid amides; benzamide, stearic anilide, acetoacetic anilide, thioacetoanilide; esters such as dimethyl phthalate, dibenzyl terephthalate, dibenzyl isophthalate; diethers of bisphenol S such as 4,4'-dimethoxydiphenylsulfonate, 4-iso-propoxy-4'-n-butoxydiphenylsulfone, 4,4'-dibutoxydiphenylsulfone,4,4'-di-n-(or iso-) pentyloxydiphenylsulfone and the like; diphenylamine, carbazole, 2,3-di-m-tolylbutane, 4-benzylbiphenyl, 4,4'-dimethylbiphenyl and di-$\beta$-naphthylphenylenediamine.

The dispersing agents include, for example, sulfosuccinic acid esters such as dioctyl sodium sulfosuccinate; sodium dodecylbenzenesulfonate; sodium lauryl sulfonate; and salts of fatty acid. The colored image stabilizers include, for example, salicyclic acid derivatives, metal salts (particularly zinc salt) of oxynaphthonic acid derivatives and other water-insoluble zinc compounds. The antioxidants include, for example, 2,2'-methylenebis(4-methyl-6-tert-butylphenol), 2,2'-methylenebis(4-ethyl-6-tert-butylphenol), 4,4'-propyl-methylene-bis(3-methyl-6-tert-butylphenol) and 4,4'-thiobis(2-tert-butyl-5-methylphenol). The desensitizers include, for example, aliphatic higher alcohols, polyethylene glycol and guanidine derivatives. The anti-tack agents include, for example, stearic acid, zinc stearate, calcium stearate, carnauba wax, paraffin wax and ester wax, etc.

The fluoran compound of this invention can be used for heat-sensitive transfer in accordance with such procedures as disclosed in Japanese Patent L-O-P publns. Nos. 212985/1983, 33185/1984, 42995/1985 or 225986/1984, for electro thermo-sensitive recording in accordance with such procedures, for example, as disclosed in Japanese Patent L-O-P Publns. Nos. 96137/1973, 101935/1973 or 11344/1974, and for electrophotography in accordance with such procedures, for example, as disclosed in Japanese Patent L-O-P Nos. 24530/1977 or 56932/1977.

The fluoran compound of this invention can be used, furthermore, for photosensitive recording in accordance with such procedures, for example, as disclosed in Japanese Patent Publns. Nos. 24188/1963, 10550/1970 and 45978/1975, Japanese Patent L-O-P Publns. Nos. 80120/1975, 126228/1975, 141633/1975 or 147829/1979; for ultrasonic wave recording in accordance with a procedure as disclosed in French Pat. No. 2,120,922; for electrostatic recording in accordance with a procedure as disclosed in Japanese Patent Publn. No. 3932/1974; and in photosensitive printing materials in accordance with a procedure as disclosed in Japanese Patent L-O-P Publn. No. 12104/1973.

In addition to the applications as mentioned above, the fluoran compound of this invention can also be used as a color forming component in a composition which color change occurs reversibly (color⇌colorless) under the influence of temperature as disclosed, for example in Japanese Patent L-O-P Publns. Nos. 75991/1975 and 219289/1985, by using in admixture therewith one or more compounds selected from a compound having a phenolic hydroxyl group and the metal salts thereof, an aromatic carboxylic acid and the metal salts thereof, an aliphatic carboxylic acid of 2 to 5 carbon atoms and the metal salts thereof, and an acid phosphoric ester and the metal salts thereof, and one or more compounds selected from alcohols, esters, ketones, ethers and acid amides. The compound having a phenolic hydroxyl group includes the phenolic compounds used as the color developer in the heat-sensitive recording papers or the phenol resins used as the color developer in the pressure-sensitive recording papers, but not limiting thereto. Also, the metal salts of said compound include salts of calcium, magnesium, zinc, aluminium, tin, titanium, etc., but not limiting thereto. The aromatic and aliphatic carboxylic acids include benzoic acid, toluic acid, p-tert.-butylbenzoic acid, chlorobenzoic acid, gallic acid, phthalic acid, naphthoic acid, maleic acid, fumaric acid, and the like, and the metal salts thereof include salts of calcium, magnesium, zinc, aluminum, tin, titanium and the like, but not limiting thereto. The acid phosphoric ester includes those in which a phosphate group is attached to an alkyl group which may be branched, an alkenyl group, an alkynyl group, a cycloalkyl group and an aryl group, and the derivatives thereof. The alcohols include a monohydric alcohol such as octyl alcohol, nonyl alcohol, decyl alcohol, lauryl alcohol, myristyl alcohol, cetyl alcohol, palmityl alcohol, stearyl alcohol, dococyl alcohol, oleyl alcohol and benzyl alcohol, and a polyhydric alcohol such as ethylene glycol, diethylene glycol, polyethylene glycol, polypropylene glycol, pentaerythritol and sorbitol. The esters include methyl stearate, butyl stearate, triglyceride of 12-hydroxystearic acid, lauryl myristate, octyl caproate, insect wax and the like. The ketones include diisobutyl ketone, acetophenone, diphenyl ketone and the like. The acid amides include caprylamide, laurylamide, myristylamide, palmitylamide, stearylamide, oleylamide, stearylanilide and the like, but not limiting thereto.

The following examples (preparative and use examples) and comparative examples are presented, but the present invention is not limited thereto.

EXAMPLE 1

(Preparative Example)

A 300 ml flask was charged with 161 g of conc. sulfuric acid and 161 g of o-(4-N-isobutyl-ethylamino-2-hydroxybenzoyl)benzoic acid and 21.3 g of 4-ethoxydiphenylamine were added, and the reaction was continued at temperatures of 20° to 25° C. for 48 hours. The reaction solution was poured into 450 g of iced water, crystals precipitated was removed by filtration, washed with water, heated while stirring together with 385 ml of toluene, 115 ml of water and 38.5 g of caustic soda and refluxed for 2 hours. The solution was allowed to cool, the aqueous phase was removed, the toluene phase was washed with hot water, a slight amount of insoluble matter was filtered out and about 250 ml of toluene was distilled off. The residual solution was cooled, cyrstals precipitated was removed by filtration and washed with toluene and dried to yield 36.8 g of 3-N-isobutyl-ethylamino-7-phenylaminofluoran as substantially colorless crystals, m.p. 171°–171.8° C.

EXAMPLE 2

(Pressure-sensitive copying paper)

4.0 g of 3-N-isobutyl-ethylamino-7-phenylaminofluoran were mixed with 50.0 g of alkyl diphenylmethane (Hizole SAS 296 manufactured by Nisseki Kagaku K.K.) and 36.0 g of diisopropyl naphthalene (KMC-113 manufactured by Kureha Kagaku K.K.), heated to dissolve, stirred at 90° C. for 10 minutes and cooled (Solution A).

Separately, 30.0 g of a 10% aqueous solution of a sulfonic acid-modified polyvinyl alcohol (Gosenol CKS-50, produced and sold by The Nippon Synthetic Chemical Industry Co., Ltd., average polymerization degree about 300, saponification degree 97%, and modification degree 10 mol %), 15.0 g of a 10% aqueous solution of ethylene-maleic anhydride copolymer (EMA-31, produced and sold by Monsanto Co.) and 67.5 ml of water were mixed and added with further 5.0 g of urea and 0.5 g of resorcinol to prepare a solution. The solution was adjusted to pH 3.4 with a 20% aqueous caustic soda solution (Solution B).

Solution A was added to Solution B and stirred with a homomixer at 9,000 rpm for 2 minutes to prepare an emulsion. The emulsion was then charged with 14.0 g of a 35% aqueous formalin solution and stirred at 9,000 rpm for 3 minutes. Thereafter, the emulsion was stirred at 8000 rpm and elevated temperatures of 60°–65° C. for 60 minutes. The stirring with the homomixer was ceased, the emulsion was cooled to 40° C. and adjusted to pH 7.5 with the addition of 28% ammonia water to prepare a suspension of microcapsules.

27.0 g of this suspension (kept at a temperature below 30° C.), 3.5 g of wheat starch, 8.5 g of an 8% wheat starch solution and 34.0 ml of water were mixed and stirred with a stirrer at room temperatures for 30 minutes to prepare a coating solution.

The coating solution was coated with a wire bar No. 12 on a white paper and dried for 3 minutes with air kept at 60° C. to prepare a top sheet of pressure-sensitive copying paper.

A coated surface of the top sheet as prepared above was superposed on a coated surface of a bottom sheet which was prepared by coating phenole-formalin resins onto paper and drying it. The superposed sheets were pressed at a pressure of 20 kg/cm$^2$ between two rolls, whereby a slightly blackish green color developed on the coated surface of the bottom sheet.

Further, the coated surface of the top sheet was irradiated over carbon arc fade-o-meter for 60 minutes. Then, a color was developed on the bottom sheet in the same manner as mentioned above. The developed color was slightly paled green as compared with the case where the coated surface of the top sheet was not irradiated, but no change in hue was observed.

The data on the developed colors as measured by a color difference meter are as shown in Table 1 above.

COMPARATIVE EXAMPLE 1

The top sheet for pressure-sensitive copying paper was prepared according to the same procedure as described in Example 2, but 3-diethylamino-5-methyl-7-dibenzylaminofluoran (Compound A) and 3-pyrrolidino-7-phenylaminofluoran (Compound B) were substituted for 3-N-isobutyl-ethylamino-7phenylaminofluoran used in Example 2.

Following the same procedure as described in Example 2, a color was developed on the coated surface of the bottom sheet for pressure-sensitive copying paper. The color developed by Compound A was bright green and the color developed by Compound B was of the same hue as that shown in Example 2, but slightly higher density.

Alternatively, the coated surfaces of these two kinds of top sheets were irradiated with carbon arc and these surfaces were superposed on the coated surface of the bottom sheet to develop colors, in the same manner as described in Example 2.

The color developed by Compound A was pale reddishbrown color. The color developed by Compound B was very paled green.

The data as measured by a color difference meter on the developed surface are as shown in Table 1 above.

EXAMPLE 3

(Pressure-sensitive copying paper)

There were mixed 6.0 g of 3-N-isobutyl-ethylamino-7-phenylaminofluoran, 2.0 g of 3-N-isobutyl-ethylamino-6-methyl-7-chlorofluoran (vermilion color former), 0.5 g of crystal violet lactone (blue color former) and 0.5 g of benzoyl leucomethylene blue (blue color former). 1.0 g of this mixture was dissolved in 20 g of alkyl naphthalene at 90° C. to obtain a solution (Solution A). Separately, 2.0 g of gelatin (isoelectric point 8.0) and 0.5 g of carboxymethyl cellulose were completely dissolved in 120 ml of water to obtain a solution (Solution B). Subsequently, Solutions A and B were mixed at 50°-60° C., and stirred at high speed to emulsify, and the emulsified product was adjusted to pH 8.5-9.0. Thereafter, the emulsified product was stirred at high speed for 20 minutes, the pH was gradually lowered to pH 3.8 with dilute acetic acid, and cooled with stirring to 5°-10° C. To the cooled emulsified product was added 6 g of a 37% aqueous formalin solution, and the mixture was stirred at 10°-20° C. for further 1 hour.

Subsequently, the emulsion was adjusted to pH 9.0 with an aqueous sodium hydroxide solution (5%). This emulsion was gently stirred for several hours to obtain an emulsion containing very fine microcapsules covered with gel films of carboxymethyl cellulose and geleatin, each capsule containing inside an alkyl naphthalene solution of the mixture of four color formers. This emulsion was coated on a paper and dried to prepare a top sheet of pressure-sensitive paper. Separately, phenol-formalin resin was coated on a paper and dried to prepare a bottom sheet. The coated surface of the top sheet was placed on the coated surface of the bottom sheet, and letters were written on the uncoated surface of the top sheet, whereby deep black-colored letters appeared very quickly on the coated surface of the bottom sheet.

With the bottom sheet for pressure-sensitive copying paper coated with clay in place of the phenolformalin resin, deep black-colored letters appeared likewise.

EXAMPLE 4

(Pressure-sensitive copying paper)

A mixture of four color formers was prepared by substitution of 4.0 g of 3-cyclohexylamino-6-chlorofluoran for 2.0 g of 3-N-isobutyl-ethylamino-6-methyl-7-chlorofluoran used in Example 3. 1.0 g of the mixture was used to prepare a pressure-sensitive copying paper in the same way as described in Example 3. The pressure-sensitive copying paper was subjected to the same procedure as mentioned in Example 3, whereby black-colored letters appeared likewise.

EXAMPLE 5

(Heat-sensitive recording paper)

3.5 g of 3-N-isobutyl-ethylamino-7-phenylaminofluoran, 41.5 g of a 15% aqueous solution of polyvinyl alcohol (KURARAY-105 manufactured by Kuraray Co., Ltd.), 15.0 g of clay (UW-90 manufactured by Engelhard) and 40.0 g of water were charged, together with 150 g of glass beads (1–1.5 mm in diameter), into a 250 ml polyethylene bottle, the bottle was sealed and placed to a paint conditioner manufactured and sold by Red Devil Co. The bottle was shaken at a rate of 630 times/min for 5 hours, and thereafter the beads were removed to obtain an aqueous suspension of the above two fluoran compounds (suspension A).

Separately, 10.5 g of bisphenol A as a color developer, 41.5 g of a 15% aqueous solution of polyvinyl alcohol (same as above), 8.0 g of clay (same as above) and 40.0 g of water were charged, together with 150 g of glass beads (same as above), into a 250 ml polyethylene bottle, and the bottle was sealed. The bottle was shaken with the paint conditioner at a rate of 630 times/min for 8 hours, and the glass beads were removed therefrom to prepare an aqueous suspension of bisphenol A (suspension B).

The suspensions A and B, each 10 g, were mixed together, and the mixture was stirred for 20 minutes to prepare a coating liquid.

This coating liquid was coated with wire rod No. 12 onto a white base paper and dried for 2 minutes with air kept at 60° C. to prepare a heat-sensitive recording paper. The coated surface of the heat-sensitive recording paper was found a slightly greenish white color.

The coated surface of the heat-sensitive recording paper was heated (1 kg/cm$^2$) with a heat gradient tester (manufactured by Toyo Seiki Seisakusho K.K.) at a temperature of 150° C. for 5 seconds, thereby to develop color. The color hue was slightly blackish dark green.

The heat-sensitive recording papers before and after color development by heating were stored for 24 hours in a container kept at 50° C. and 80% RH (moisture and heat resistance test) and they were taken out of the container for visual inspection, whereupon no substantial change in tone of colors of the coated surface of both papers was observed.

Furthermore, the coated surfaces before and after color development were exposed to sunlight for 10 hours, whereupon change in whiteness of the coated surface before color development was slight, and the color developed surface did not change so much in hue as well as in color density.

The above-mentioned coated surfaces were measured in whiteness and in developed color density by means of a MacBeth densitometer RD-515, and the measured values were shown, together with the measured values obtained similarly in the following Comparative Example 2, in Table 2.

COMPARATIVE EXAMPLE 2

Heat-sensitive recording papers were preapred in substantially the same manner as in Example 5 except that in place of 3-N-isobutyl-ethylamino-7-phenylfluoran used in Example 5, there was used in each case compound A and compound B.

In comparison with the coated surface of the heat-sensitive recording paper of Example 5, each coated surface of the heat-sensitive recording papers as prepaed above was found more greenish though to a slight extent.

The coated surfaces of the heat-sensitive recording papers prepared above were allowed to develop color by heating in the same manner as in Example 5, whereupon the color developed by compound A was green but more pale than the color developed by the present compound, and the color developed by compound B was slightly blackish dark green which was slightly paler than the color developed by the present compound.

These heat-sensitive recording papers were subjected to the moisture and heat resistance test and to the light fastness test in the same manner as in Example 5.

Upon the moisture and heat resistance test, the coated surfaces before color development in which compounds A and B were used respectively were found to proceed in coloration to a lightly appreciable extend in comparison with the case of the present compound. In the light fastness test, the coated surface using compound A was found a pale brown color, and the coated surface using compound B was found a slightly brownish yellow color.

In the moisture and heat resistance test, the colors developed by heating on the coated surfaces containing compounds A and B, respectively, did not change so much in tone, whereas in the light fastness test, a color developed on the coated surface by compound A changed from green to dark brown, and a slightly blackish green color developed on the coated surface by compound B was markedly faded in comparison with the green color developed by the present compound.

The data as measured on these heat-sensitive recording papers are as shown in Table 2.

EXAMPLE 6

(Heat-sensitive recording paper)

A heat-sensitive recording paper was prepared and color developed according to the same procedure as described in Example 5, but substituting 3.5 g of a mixture of 1.0 g of 3-N-isobutyl-ethylamino-7-phenylaminofluoran and 9.0 g of 3-N-methyl-cyclohexylamino-6-methyl-7-phenylaminofluoran (black color former) for 3.5 g of 3-N-isobutyl-ethylamino-7-phenylaminofluoran used in Example 5. The color hue was beautiful black. The color developed surface was exposed to sunlight for 5 hours. No marked change was observed in the color hue.

In passing, a heat-sensitive recording paper was prepared in the same manner, as mentioned above by using 3.5 g of 3-N-methyl-cyclohexylamino-6-methyl-7-phenylaminofluoran alone. The recording paper was color-developed in the same procedure as mentioned above, whereby the color hue was slightly reddish black.

What is claimed is:

1. A color forming record material which comprises a substrate, an acidic substance and 3-N-isobutyl-ethylamino-7-phenylaminofluoran as a color former.

2. The record material of claim 1 which is a heat-sensitive recording paper.

3. The record material of claim 1 which is a pressure-sensitive copying paper.

4. The record material of any of claims 1-3 which further comprises a black color former.

5. The record material of any of claims 1-3 which further comprises at least one of a red color former and a blue color former.

* * * * *

UNITED STATES PATENT AND TRADEMARK OFFICE
CERTIFICATE OF CORRECTION

PATENT NO. : 4,668,967
DATED : May 26, 1987
INVENTOR(S) : Masakichi YAHAGI et al It is certified that error appears in the above-identified patent and that said Letters Patent is hereby corrected as shown below:

Column 3, line 21, "ract" should read --fact--.

Column 4, line 41, "o-(4-N-isobutyl-ethylamino-2-hydroxy)benzoylbenzoic" should read -o-(4-N-isobutyl-ethylamino-2-hydroxybenzoyl)benzoic--.

Column 7, line 28, "(2,2dimethylbenzyl)" should read --(2,2-dimethylbenzyl)--.

Column 8, line 28, "dimethoxydiphenylsulfonate" should read --dimethoxydiphenylsulfone--.

Column 9, line 61, "161 g" should read --34.1 g--.

Signed and Sealed this

Sixteenth Day of August, 1988

Attest:

DONALD J. QUIGG

Attesting Officer    Commissioner of Patents and Trademarks